US009712318B2

(12) United States Patent
Foerster et al.

(10) Patent No.: US 9,712,318 B2
(45) Date of Patent: Jul. 18, 2017

(54) DATA SYNCHRONIZATION METHOD AND DATA TRANSMISSION SYSTEM TO CARRY OUT SUCH A METHOD

(71) Applicant: COMMISSARIAT A L'ENERGIE ATOMIQUE ET AUX ENERGIES ALTERNATIVES, Paris (FR)

(72) Inventors: Michael Foerster, Gradignan (FR); Guillaume Charvet, Sassenage (FR); Jean Porcherot, Grenoble (FR)

(73) Assignee: Commissariat a l'Energie Atomique et aux Energies Alternatives, Paris (FR)

( * ) Notice: Subject to any disclaimer, the term of this patent is extended or adjusted under 35 U.S.C. 154(b) by 370 days.

(21) Appl. No.: 13/859,900

(22) Filed: Apr. 10, 2013

(65) Prior Publication Data

US 2013/0293393 A1    Nov. 7, 2013

(30) Foreign Application Priority Data

Apr. 10, 2012 (FR) ...................................... 12 53266

(51) Int. Cl.
*H04L 7/04* (2006.01)
*A61B 5/0484* (2006.01)
(Continued)

(52) U.S. Cl.
CPC .............. *H04L 7/04* (2013.01); *A61B 5/0006* (2013.01); *A61B 5/0484* (2013.01); *H04L 7/0008* (2013.01)

(58) Field of Classification Search
CPC ....... H04L 7/04; H04L 7/0008; A61B 5/0006; A61B 5/0484
(Continued)

(56) References Cited

U.S. PATENT DOCUMENTS 6,366,805 B1    4/2002  Lutz
7,280,550 B1 *  10/2007  Rosenboom .......... H04J 3/0682
                                                        370/404
(Continued)

FOREIGN PATENT DOCUMENTS

WO        01/06922       2/2001

OTHER PUBLICATIONS

French Search Report for Applicaiton No. 1253266 dated Feb. 5, 2013.

*Primary Examiner* — Joseph Feild
*Assistant Examiner* — Omar Casillashernandez
(74) *Attorney, Agent, or Firm* — Morgan, Lewis & Bockius LLP

(57) ABSTRACT

A method for synchronizing data transmitted between at least one transmit terminal (TE) and a receive terminal (TR) via a transmission channel ($C_D$) with unmanaged latency, comprising the steps:
  (a) in said or in each transmit terminal, generating at least one synchronization signal ($S_{SYNC}$) having a known temporal relationship with the time of transmission of at least one data packet ($S_{EEG}$) to be synchronized;
  (b) transmitting said or each data packet to be synchronized on said transmission channel with unmanaged latency, and said or each synchronization signal on an auxiliary transmission channel ($C_S$) with managed latency;
  (c) in said receive terminal, receiving said or each data packet to be synchronized and said or each synchronization signal; and
  (d) synchronizing said or each data packet received by said receive terminal by means of said synchronization signal.

Data acquisition device for carrying out such a method.

16 Claims, 5 Drawing Sheets

(51) Int. Cl.
*A61B 5/00* (2006.01)
*A61B 5/04* (2006.01)
*H04L 7/00* (2006.01)

(58) Field of Classification Search
USPC .................................................. 340/870.18
See application file for complete search history.

(56) References Cited

U.S. PATENT DOCUMENTS

| | | | |
|---|---|---|---|
| 2002/0188330 A1* | 12/2002 | Gielen et al. | 607/45 |
| 2004/0010623 A1* | 1/2004 | Sher et al. | 709/248 |
| 2009/0062676 A1* | 3/2009 | Kruglikov et al. | 600/544 |
| 2009/0131762 A1* | 5/2009 | Pelzek et al. | 600/301 |
| 2009/0274326 A1* | 11/2009 | Jia et al. | 381/311 |
| 2011/0172504 A1* | 7/2011 | Wegerich | 600/301 |
| 2011/0288605 A1* | 11/2011 | Kaib et al. | 607/5 |
| 2013/0101061 A1* | 4/2013 | Clevorn | H04W 52/241 375/285 |

* cited by examiner

DATA SYNCHRONIZATION METHOD AND DATA TRANSMISSION SYSTEM TO CARRY OUT SUCH A METHOD

BACKGROUND

The invention relates to a method for synchronizing data transmitted between at least one transmit terminal and a receive terminal via a transmission channel with unmanaged latency. It also relates to a data transmission system to carry out such a method.

The invention enables notably the synchronization of the signals originating from a sensor or a set of sensors connected to a central unit via wireless links. It applies notably to the acquisition of biological, and more particularly neuronal, signals.

Biological signal acquisition systems have existed for a long time, but it is only recently that miniaturization has enabled the development of wireless acquisition systems. Conventional wired systems, such as EEG measuring caps, for example, physically connect the sensor(s) close to or in contact with a person or an animal ("the patient") to measurement electronics, which are in turn connected by cable to a data processing unit, which may notably be a computer. Conversely, wireless systems integrate the acquisition electronics at the location of the measurement and transmit the data to the data processing unit via a wireless communication means.

During the acquisition of biological signals, one of the main subjects of study is the influence of external parameters on the measured quantities. In the neurosciences, for example, attempts are made to detect variations in the electroencephalography (EEG) signals in response to a sensory stimulus (flash of light, calling of first name, etc.). To do this, it is necessary to synchronize the time of the sensory stimulus and the different EEG signals, i.e. to place them on a common time base.

Synchronization of the data does not pose any particular difficulty in the case of conventional systems, in which the signal acquisition sensors are connected to the data processing unit in a wired manner. It suffices in fact to use a channel of the acquisition system as the input for the stimulus. For example, the signal activating a flash can be redirected onto one of the recording channels of the acquisition system. An acquisition system of this type is shown in FIG. 1, where the reference P indicates a patient undergoing an EEG examination (only his brain is shown), DSS indicates a sensory stimuli generation device (for example a flash, a screen, a loudspeaker, etc.), SA indicates a data acquisition system, UT indicates a computer serving to control the device DSS and also to process the EEG signals acquired by the system SA. The computer UT transmits a control signal, $S_{DSS}$, which triggers the generation of a sensory stimulus by the device DSS; the response of the brain of the patient P to this stimulus is measured in the form of EEG signals, $S_{EEG}$. The signals $S_{DSS}$ and $S_{EEG}$ are acquired by respective measurement channels of the system SA and are transmitted to the computer UT. Since the propagation delays of the signals are known, or in any event constant, the latter can easily place them on a common time base.

The document WO 01/06922 describes a system of this type. In this system, a stimulation device (a video recorder) and an EEG signal analog-digital converter are simultaneously activated by means of respective electronic switches; a computer then acquires the video signals at the output of the video recorder and also the digitized EEG signals.

This approach cannot be transposed directly onto wireless acquisition systems, or, if so, only with very imprecise synchronization. In fact, wireless data transmission systems in most cases present a delay ("latency") which is relatively substantial (in the order of several hundred milliseconds), which is unknown and—above all—variable. In fact, for reasons of robustness, wireless transmission protocols generally implement sophisticated error detection and correction algorithms which may entail repeated exchanges between the receiver and transmitter. The time required to transmit a data packet therefore depends on the quality of the link (signal-to-noise ratio, interferences, etc.), the transmission speed and also the workload of the computer connected to the receiver. Thus, in wireless communication systems, the latency is not controlled (it is unknown and variable in an unforeseeable manner). This situation is illustrated by FIG. 2, which shows an acquisition system comprising two separate acquisition systems: a first, $SA_1$, intended for the acquisition of the signal $S_{EEG}$ and comprising a transmit terminal TE connected to a receive terminal TR via a wireless link $C_D$; and a second, $SA_2$, intended for the acquisition of the signal $S_{DSS}$. The two acquisition systems do not communicate with one another (or, if so, only via a wireless link with unmanaged latency). Consequently, it is not possible to locate the signals $S_{EEG}$ and $S_{DSS}$ on a common time base, except by ignoring the latency of the wireless link (or assuming it to be constant), which entails substantial synchronization errors.

SUMMARY OF THE INVENTION

The invention aims to overcome the aforementioned disadvantages of the prior art and enable the synchronization of data transmitted between a transmit terminal (or a plurality thereof) and a receive terminal via a transmission channel with unmanaged latency.

One subject-matter of the invention enabling this object to be achieved is a method for synchronizing data transmitted between at least one transmit terminal and a receive terminal via a transmission channel with unmanaged latency, comprising the steps consisting in:

a) in said or in each transmit terminal, generating at least one synchronization signal having a known temporal relationship with the time of transmission of at least one data packet to be synchronized;

b) transmitting said or each data packet to be synchronized on said transmission channel with unmanaged latency, and said or each synchronization signal on an auxiliary transmission channel with managed latency;

c) in said receive terminal, receiving the said or each data packet to be synchronized and the said or each synchronization signal; and d) synchronizing said or each data packet received by said receive terminal by means of the said synchronization signal.

Both said transmission channel and said auxiliary transmission channel may be wireless transmission channels. However, the auxiliary transmission channel may have a low transmission speed and tolerate the relatively high error rate, thus allowing a simple communication protocol to be used, providing management of the latency to the detriment of capacity and robustness.

According to different embodiments of the method of the invention:

said or each transmit terminal may transmit a plurality of data packets to be synchronized as well as a said synchronization signal in correspondence with each said data packet to be synchronized. In this case, it may be provided to introduce identification information into each said data packet to be synchronized, enabling said packet to be associated with the corresponding synchronization signal.

Alternatively, said or each transmit terminal may transmit a plurality of data packets to be synchronized, as well as a synchronization signal every N said data packets, where N>1, said data packets to be synchronized then being transmitted at a more or less constant frequency at least over a period between the transmission of two consecutive synchronization signals. In this case, it may be provided to introduce identification information into each data packet in correspondence with which a synchronization signal is transmitted, enabling said packet to be associated with the corresponding synchronization signal. It may also be provided to introduce information into each said data packet to be synchronized, enabling the order in which said packets have been transmitted to be determined.

Alternatively, said or each transmit terminal may transmit a single synchronization signal during a data transmission session. This embodiment assumes that the clock frequencies of the transmit terminal(s) or the receive terminal are identical, or in any case known and having negligible drifts.

The said or each data packet to be synchronized may notably represent a signal acquired by a sensor or set of sensors associated with said or with a said transmit terminal. More particularly, the said or each data packet to be synchronized may represent a neuronal signal generated by a patient in response to a sensory stimulus, said synchronization step d) comprising the location of the said or of each said data packet and said stimulus on a common time base.

Another subject-matter of the invention is a data acquisition system comprising:

at least one transmit terminal, to transmit at least one data packet on a transmission channel; and a receive terminal, to receive said or each data packet via said transmission channel;

said transmission channel having unmanaged latency;

characterized in that:

said or each transmit channel is suitable for transmitting, on an auxiliary transmission channel with managed latency, at least one synchronization signal having a known temporal relationship with the time of transmission of said or of at least one said data packet; and in that said receive terminal is suitable for receiving said or each data packet to be synchronized and said or each synchronization signal, and for synchronizing said or each data packet received by means of said synchronization signal.

According to different embodiments of the invention:

Both said transmission channel and the said auxiliary transmission channel may be wireless transmission channels.

The said or each transmit terminal may be suitable for transmitting a said synchronization signal in correspondence with each said data packet.

Alternatively, said or each transmit terminal may be suitable for transmitting a plurality of data packets to be synchronized and also a synchronization signal every N said data packets, where N>1, said data packets to be synchronized being transmitted at a more or less constant frequency at least over a period between the transmission of two consecutive synchronization signals.

The acquisition system may also comprise a sensor or set of sensors associated with said or each said transmit terminal, said or each data packet transmitted by said or each transmit terminal representing a signal acquired by the corresponding sensor or set of sensors.

The acquisition system may also comprise a sensory stimulation device of a patient, and moreover:

said or each sensor or set of sensors may be suitable for acquiring neuronal signals representing the response of a patient to a sensory stimulus produced by said stimulation device; and said receive terminal may be suitable for locating said or each said data packet and said stimulus on a common time base.

DETAILED DESCRIPTION

Figure 3:
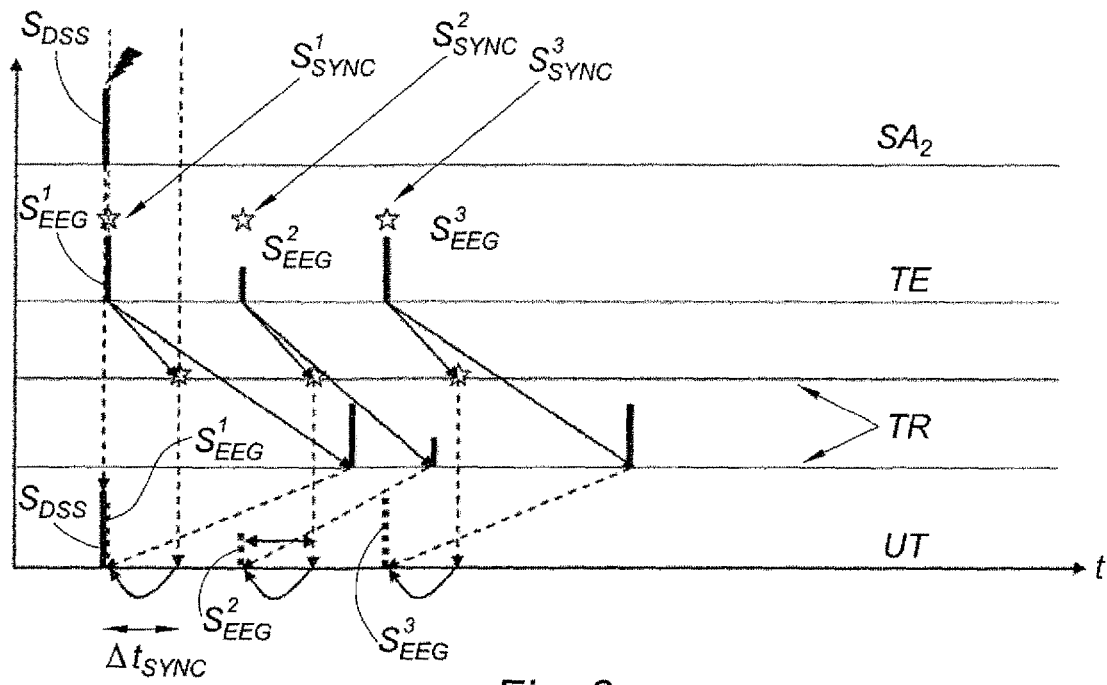
FIG. 3 shows in a general manner the principle on which the data synchronization method forming the subject-matter of the invention is based.
Figure 4:
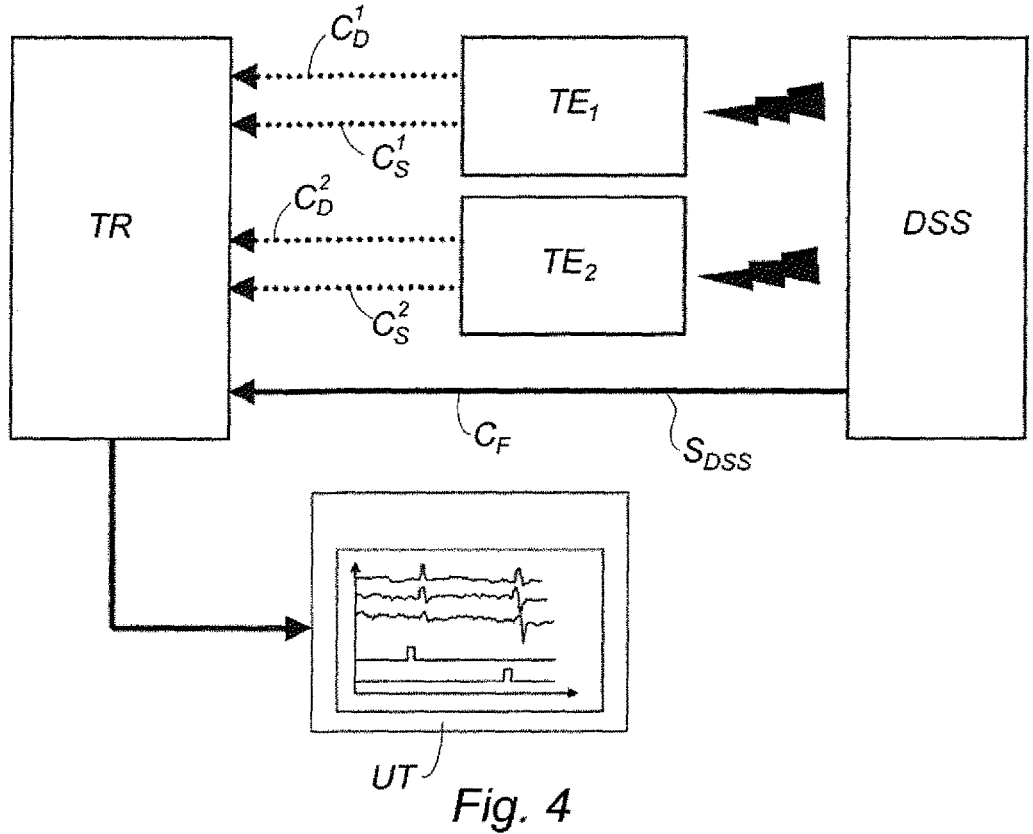
FIG. 4 shows the architecture of a data acquisition system comprising two acquisition terminals TE1 and TE2, connected to EEG headsets and linked to a single receive terminal TR via wireless connections.
Figure 5:
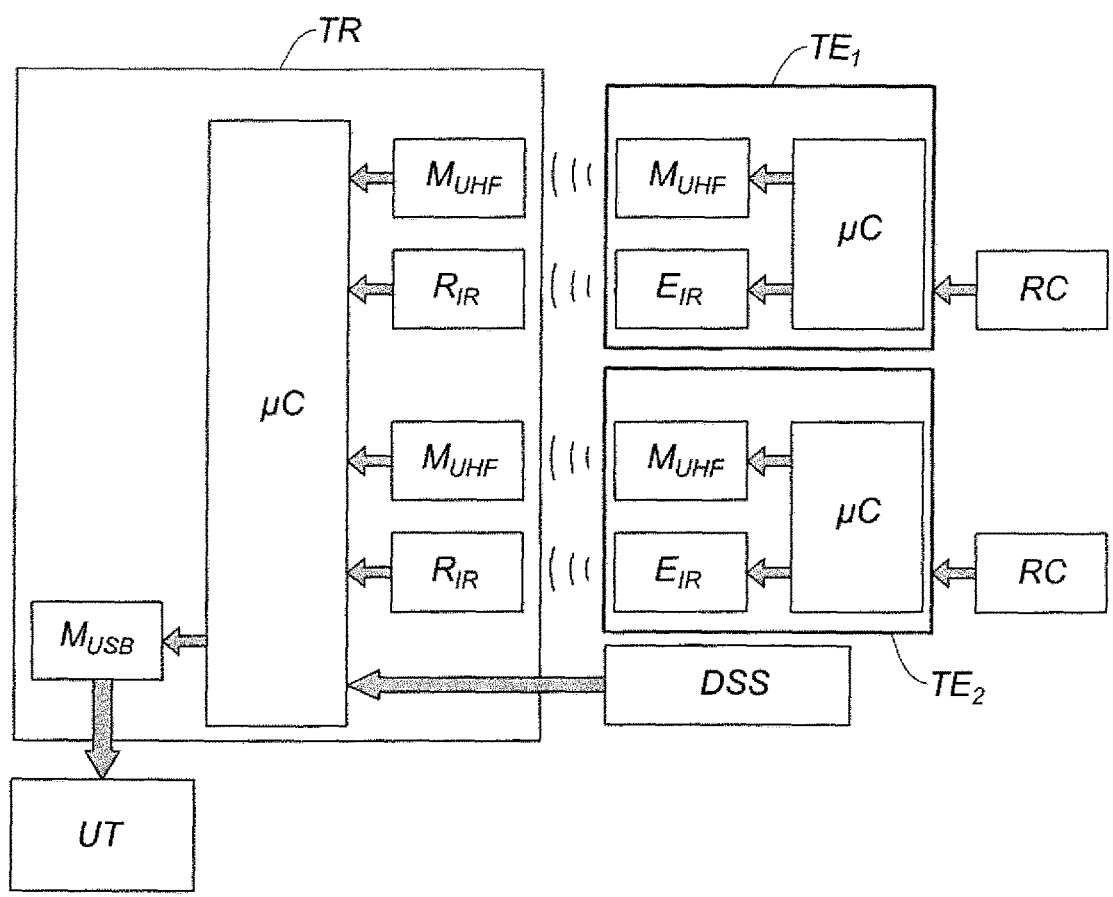
FIG. 5 shows the architecture of the acquisition system shown in FIG. 4 in more detail.
Figure 6:
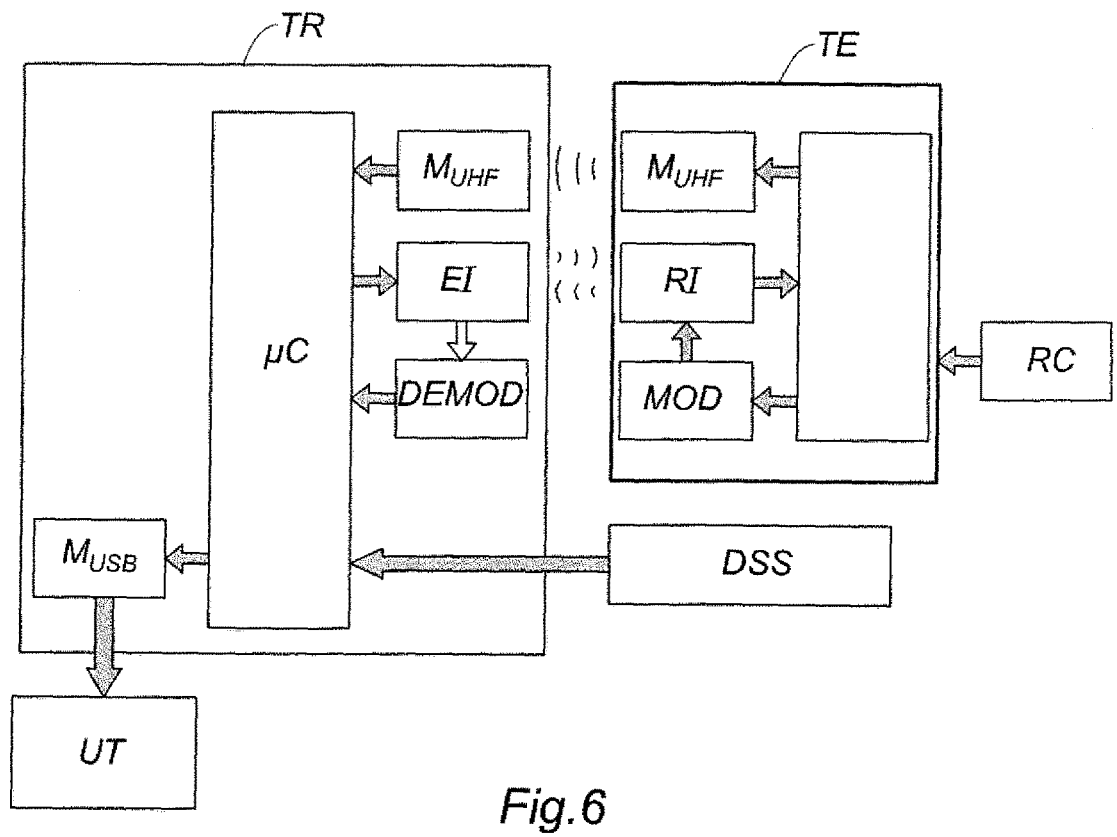
FIG. 6 shows the architecture of a data acquisition system using a transmit terminal implanted in the body of a patient.
Figure 7:
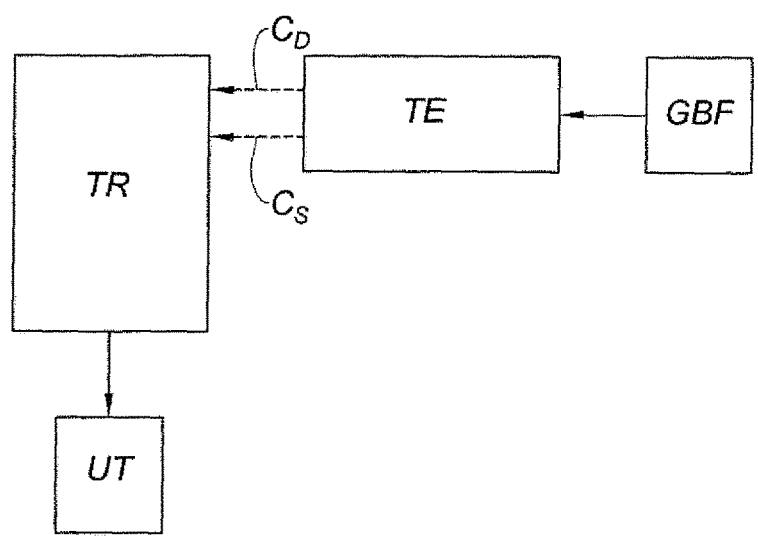
FIG. 7 illustrates the experimental validation of a data synchronization method according to the invention.
Figure 8:
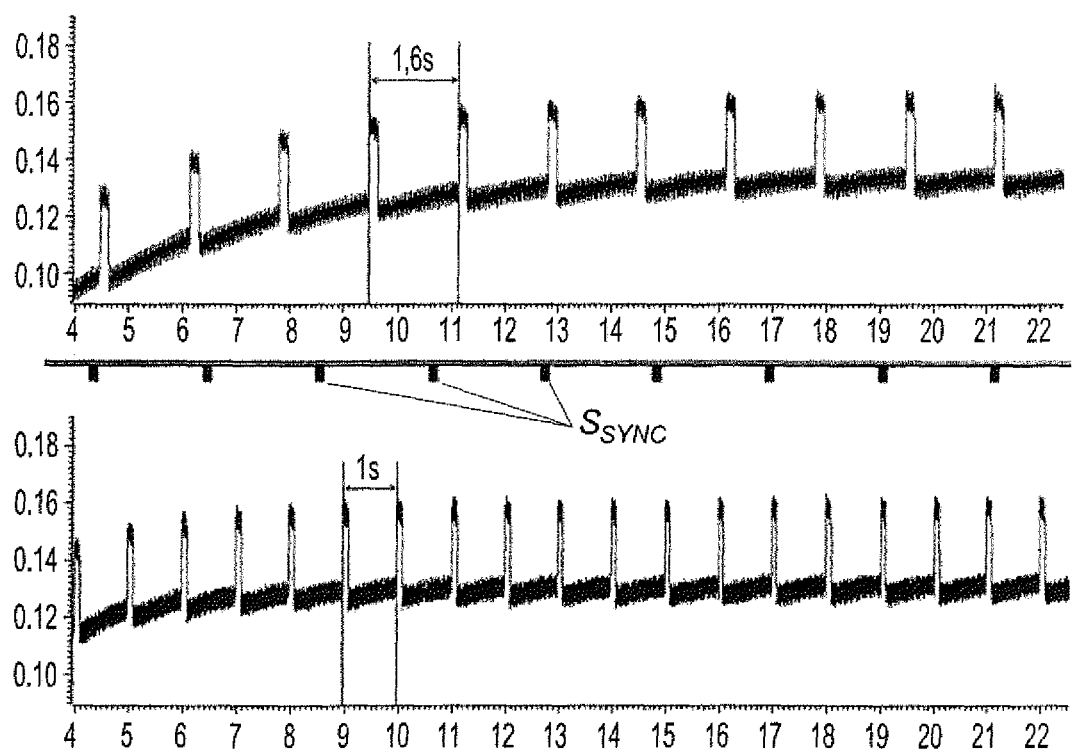
FIG. 8 illustrates the experimental validation of a data synchronization method according to the invention. The upper panel shows the waveform of the pulse signal reconstructed by the data processing unit. The lower panel shows that the application of a synchronization method according to the invention enables a correct reconstruction of the pulse signal.

Other characteristics, details and advantages of the invention will be revealed from a reading of the description, with reference to the attached drawings provided by way of example, in which:

FIG. 3 shows in a general manner the principle on which the data synchronization method forming the subject-matter of the invention is based;

FIGS. 4 to 6 are functional diagrams of data acquisition systems according to different embodiments of the invention; and FIGS. 7 and 8 illustrate the experimental validation of a data synchronization method according to the invention.

As explained above, a robust wireless transmission channel has a variable latency due to the use of a communication protocol intended to ensure the integrity of the transmitted data (error detection and correction, dispatch of acknowledgements of receipt, etc.) and delays within the processing unit implementing the acquisition of said data. In order to perform the synchronization of the transmitted signals, and therefore locate them on a common time base, the present invention provides for the use of an auxiliary transmission channel, similarly wireless but having managed latency. This auxiliary channel does not necessarily have to present substantial robustness and/or capacity as it is used only to transmit a synchronization signal—in most cases a simple code—at the same time as a data packet to be synchronized (or, more generally, with a known temporal relationship with the time of transmission of this packet). As the latency of the auxiliary channel is known, the knowledge of the time of reception of the synchronization signal allows its transmission time, and therefore that of the data packet, to be determined.

This operating principle is shown in FIG. 3. This figure refers to a system similar to that shown in FIG. 2, but supplemented with the addition of the auxiliary channel between the transmit terminal TE and the receive terminal TR of the acquisition system $SA_1$. It will be noted that the second acquisition system $SA_2$ is connected to the processing unit UT via a wired connection, and therefore has a common time base with it (time "t").

The generation of a sensory stimulus is accompanied by the reception, by the acquisition system $SA_2$, of a signal $S_{DSS}$. This stimulus triggers a response in the patient P which is sampled and digitized. This response corresponds, for example, to a signal measured by one or more electrodes. Temporal sampling of this response generates three data packets; $S_{EEG}^1$, $S_{EEG}^2$ and $S_{EEG}^3$. A data packet is understood to mean the information resulting from the sampling of the signals produced by the electrodes at a given time. In a general manner, a data packet comprises signals transmitted simultaneously by the acquisition system.

The acquisition system $SA_1$ generates these three data packets and retransmits them on the transmission channel with unmanaged latency; at the same time, it generates three synchronization signals $S_{SYNC}^1$, $S_{SYNC}^2$, and $S_{SYNC}^3$ and transmits them on the auxiliary channel with managed latency. In general, the auxiliary channel will have neither sufficient capacity nor robustness to enable the transmission of the data packets, the reason for this being simply so that it can have a latency which is as constant as possible. The receive terminal TR receives the synchronization signals with a known delay, $\Delta t$, and the data packets with unknown delays which differ from one another; these signals are then transmitted—with information indicating their reception time—to the processing unit UT. The latter thus has all the elements enabling it to carry out the synchronization: the latency $\Delta t$ of the auxiliary channel being known, the time of transmission of the synchronization signals $S_{SYNC}^1$, $S_{SYNC}^2$, and $S_{SYNC}^3$ can be calculated; it is furthermore known that the data packets $S_{EEG}^1$, $S_{EEG}^2$ and $S_{EEG}^3$ were transmitted at the same time as said synchronization signals. These three data packets can thus be placed on a common time base, even though the transmission on the wireless communication channel had affected the existing temporal relationship between them. The signal $S_{DSS}$ can be placed on the same time base without particular difficulty, since it was acquired via a wired connection. In this way, the time of transmission of each data packet $S_{EEG}^1$, $S_{EEG}^2$ and $S_{EEG}^3$ can be determined in relation to the stimulus signal $S_{DSS}$.

Figure 1:
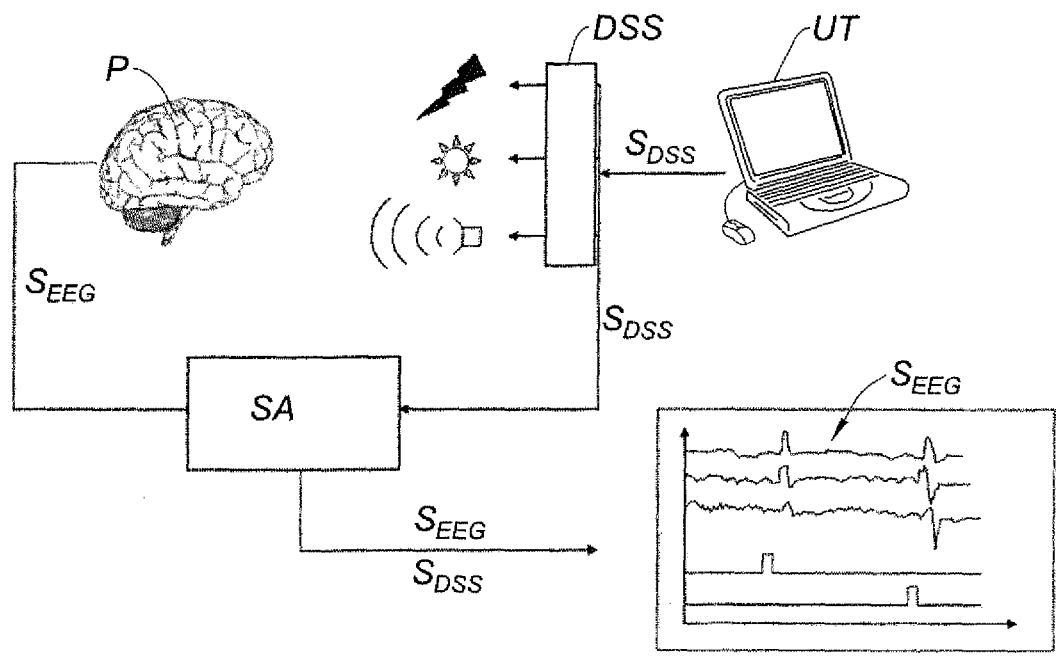
FIG. 1 shows an acquisition system, where the reference P indicates a patient undergoing an EEG examination, DSS indicates a sensory stimuli generation device, SA indicates a data acquisition system and UT indicates a computer serving to control the device DSS and also to process the EEG signals acquired by the system SA.
Figure 2:
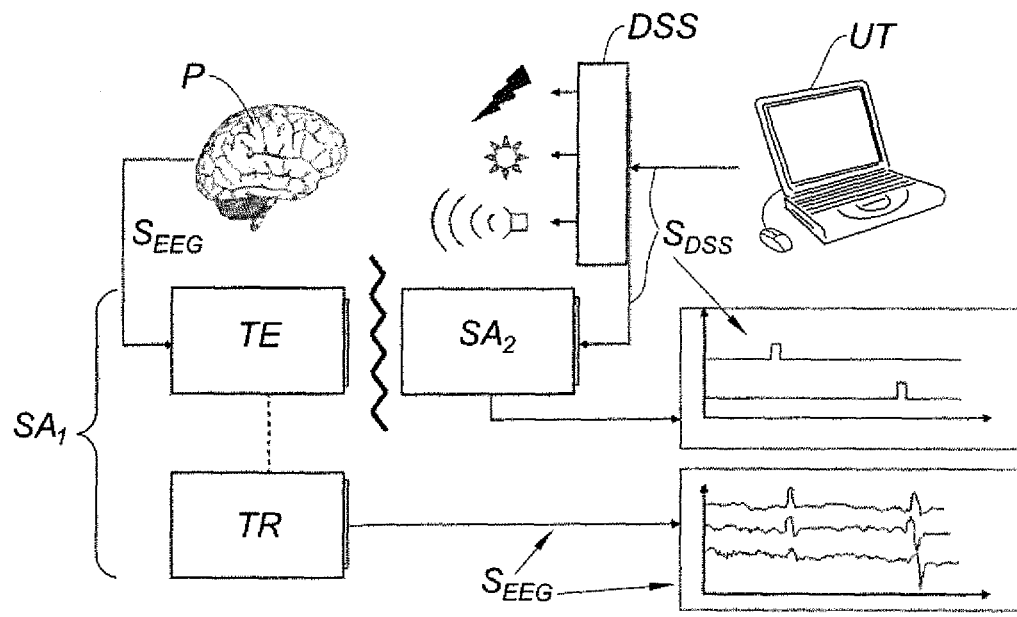
FIG. 2 shows an acquisition system comprising two separate acquisition systems SA1 and SA2.

It will be noted that the performance of the method according to the invention does not require substantial modification of the acquisition system shown in FIG. 2, but only the addition of an auxiliary wireless communication channel with managed latency.

In the case of FIG. 3, a synchronization signal is transmitted simultaneously to each data packet $S_{EEG}$. As the loss of a synchronization signal cannot be excluded (the auxiliary channel has relatively little robustness), it is appropriate that each data packet contains identification information, or a time stamp, enabling it to be associated with the corresponding synchronization signal. Thus, the loss of a synchronization signal only introduces an uncertainty concerning the time of transmission of a single data packet, but does not fundamentally disrupt the synchronization process. This embodiment is suitable for cases where the data packets are transmitted at an irregular frequency, in correspondence with unforeseeable events.

If the data packets are transmitted at a regular frequency—for example if they are obtained by sampling at a constant frequency $f_S$ and by digitization of an analogue signal—it will be generally preferable to transmit a synchronization signal every N packets, where N>1. For example, in the case of a sampling frequency $f_S$=1 kHz, N=60,000 can be taken, corresponding to the transmission of one synchronization signal per minute. In fact, the maximum admissible value of N depends essentially on the stability of the sampling frequency $f_S$, which is assumed to be constant between two synchronization signals.

In this second embodiment, it is appropriate for the data packets to contain:
  information allowing identification of those packets among said packets which were transmitted at the same time as a synchronization signal; and/or
  the order of transmission of said packets.

For example, each packet may contain a serial number which is incremented with each transmission up to a maximum value of N-1 before being reinitialized to zero, the packets bearing the number zero corresponding to the transmission of a synchronization signal.

Thus, the loss of a synchronization signal is easily detected, knowing the frequency at which the synchronization signal must be received. Moreover, the synchronization of the data packets can be carried out despite this loss, assuming that the frequency $f_S$ has remained more or less constant.

In fact, if the sampling frequency $f_S$ and the clock frequencies of the acquisition system $SA_2$ and of the receive terminal TR are known and stable, it suffices to synchronize the origins of the time bases by transmitting a single synchronization signal during each data acquisition session. However, in most cases, it will not be possible to ignore the drifts of the clock frequencies which, in a medical signal acquisition system, are typically in the order of 20 ppm (parts per million)=72 ms/hour, and a periodic transmission of synchronization signals will therefore be required in order to correct these drifts.

The synchronization method thus described can be used to synchronize the data originating from a plurality of transmit terminals without direct interconnection, for example associated with a plurality of wireless EEG headsets worn by respective patients. Similarly, the sensory stimulation device DSS, when it is present, can be connected to the processing unit via a wireless channel.

Thanks to the synchronization, is not necessary to provide for a simultaneous start-up of the different acquisition systems and any sensory stimulation device.

Another advantage of the method is that the quality of the wireless communication link does not influence the synchronization of the data.

FIG. 4 shows an acquisition system according to one embodiment of the invention, comprising two acquisition terminals $TE_1$ and $TE_2$, connected to EEG headsets (not shown) and linked to a single receive terminal TR via wireless connections. More precisely, each transmit terminal is connected to the receive terminal via a data transmission channel $C_D^1$, $C_D^2$, with unmanaged latency, and via an auxiliary, or synchronization, channel $C_S^1$, $C_S^2$, with managed latency. A sensory stimulation device DSS is connected to the receive terminal TR via a wired transmission channel $C_F$; the receive terminal TR is connected via a different wired transmission channel to the data processing unit UT.

The main characteristics of the system are as follows:
EEG signal sampling frequency: 1 kHz;
Size of each sample: 384 bits (32 channels, 12 bits/channel);
Data communication channels in the MICS band (402-405 MHz), Zarlink proprietary communication protocol, speed 400 kbit/s;
Synchronization channels; infrared link, IrDA protocol;
Transmission of a synchronization signal every $N=2^{16}$ samples, i.e. approx. every minute.

Each sample transmitted on the data communication channel is identified by a number incremented with each sample, which is reinitialized to zero when it has reached the value $2^{16}-1$.

FIG. 5 shows the architecture of the system shown in FIG. 4 in more detail. In this figure, it can be seen that:
Each transmit terminal comprises a microcontroller μC which receives signals from a set of sensors RC (for example EEG sensors), samples them and converts them into digital format in the form of data packets. The microcontroller also generates the synchronization signals.
Each data transmission channel is implemented by means of commercially available UHF transponders $M_{UHF}$, integrating an automatic flow control, error correction and retransmission management. These transponders, present on the transmission side and the reception side, guarantee the integrity of the data and a high speed, but with variable latency.
The one-way auxiliary synchronization channels are implemented by means of infrared transmitters ($E_{IR}$) and receivers ($R_{IR}$).
The receive terminal for its part comprises a microcontroller μC and communicates with a data processing unit (UT) by means of a USB module $M_{USB}$. This terminal also comprises a unit which communicates with the stimuli generation system DSS.

FIG. 6 shows the architecture of a data acquisition system using a transmit terminal implanted in the body (for example in the skull) of a patient.

The data transmission channel $C_D$ is implemented via UHF transponders, as in the embodiment shown in FIG. 5. Conversely, for the synchronization channel $C_S$, an inductive coupling is used which provides the remote feed of the implant, according to the radio frequency identification (RFID) label principle. This coupling is implemented by means of an inductive transmitter (antenna) EI located on the side of the receive terminal TR and an inductive receiver RI (loop) located on the side of the transmit terminal. A charge modulator MOD modulates the charge seen by the inductive transmitter according to a carrier frequency and a Manchester encoding, thus implementing an amplitude modulation on the inductive link. The transmit antenna EI is connected to a demodulation module DEMOD located on the receive terminal which reconstructs the original message. As the transmission of this message is carried out according to a predefined sequence and with constant latency, it is possible to implement the synchronization of the acquisitions originating from the implanted system with other acquisition systems connected to the same receive terminal and/or with the stimulation device.

The method according to the invention was tested by means of the experimental assembly shown in FIG. 7. This assembly comprises a low-frequency generator GBF used to generate pulses at a repetition frequency $f_R=1$ Hz. These pulses were sampled at a sampling frequency $f_S$ of which the nominal value $f_S^0$ was 600 Hz and the real value $f_S$ was regulated to 1 kHz in order to simulate the effect of a frequency drift. The sampled signals were transmitted from a transmit terminal TE to an acquisition terminal TR, connected to a computer UT by means of a wireless radio link in the MICS band (402-405 MHz) using the Zarlink proprietary protocol, at a speed of 400 kbit/s (data channel $C_D$, having an unmanaged latency). A synchronization signal $S_{SYNC}$ was generated every 2048 samples and was transmitted from the transmit terminal to the receive terminal via a one-way infrared link (IrDA protocol) with managed latency, $C_S$.

The data processing unit is programmed to acquire the data transmitted on the channel $C_D$ and reconstruct the pulse signal assuming that it was sampled at the nominal frequency $f_S^0=600$ Hz, and not the real frequency $f_S=1$ kHz. In the absence of synchronization, this results in a reconstructed signal having a pulse repetition frequency $f'_R=0.6$ Hz (instead of $f_R=1$ Hz), two rising edges of said pulses being separated by 1000/600 1.6 seconds. The upper panel of FIG. 8 shows the waveform of the pulse signal reconstructed by the data processing unit under these conditions. The lower panel of this same figure shows that the application of a synchronization method according to the invention enables a correct reconstruction of the pulse signal (interval of is between two consecutive rising edges), despite the fact that the real sampling frequency is very different from the nominal sampling frequency. The result obtained is all the more significant if the sampling frequency error has been deliberately chosen as much greater than can reasonably be expected in most real applications (660,000 parts per million—ppm).

The synchronization therefore enables:
a retiming of the transmitted digital signal, which is "aligned" with the synchronization signal;
a calculation of the real sampling frequency (the processing unit knows the number N of samples between two synchronization signals—here, 2048; the frequency $f_S$ is therefore obtained by dividing the time interval between two synchronization signals by N); and
where appropriate, a resampling of the signal received at the nominal frequency $f_S$.

The invention has been described with reference to a particular application, the acquisition of electroencephalography (EEG) signals in response to a sensory stimulus. However, it is not limited to this application alone, but concerns all cases where it is necessary to synchronize data transmitted via (not necessarily wireless) channels with unmanaged latency.

The invention claimed is:
1. A method for estimating a time of transmission of data packets transmitted between a transmit terminal (TE) and a receive terminal (TR) via a transmission channel ($C_D$), the time of transmission of data corresponding to the time at which the data is transmitted from the transmit terminal

(TE), the data propagating from the transmit terminal to the receive terminal with an unknown propagation delay, comprising the steps:

(a) in said transmit terminal, generating at least one synchronization signal ($S_{SYNC}$) having a known temporal relationship with the time of transmission of the data ($S_{EEG}$) to be synchronized;

(b) transmitting said data on said transmission channel from the transmit terminal to the receive terminal;

(c) transmitting said synchronization signal on an auxiliary transmission channel ($C_S$) from the transmit terminal to the receive terminal, the synchronization signal propagating from the transmit terminal to the receive terminal with a known propagation delay;

(d) in said receive terminal, receiving each data packet to be synchronized and the synchronization signal;

(e) synchronizing each data packet received by said receive terminal by means of said synchronization signal; and (f) estimating the time of transmission of the data using the known propagation delay of the synchronization signal and the temporal relationship of the synchronization signal with the time of the transmission.

2. The data synchronization method as claimed in claim 1, in which both said transmission channel and said auxiliary transmission channel are wireless transmission channels.

3. The data synchronization method as claimed in claim 1, in which said or each transmit terminal transmits a plurality of data packets to be synchronized, and also a said synchronization signal in correspondence with each data packet to be synchronized.

4. The data synchronization method as claimed in claim 3, in which identification information is introduced into each data packet to be synchronized, enabling said packet to be associated with the corresponding synchronization signal.

5. The data synchronization method as claimed in claim 1, in which said transmit terminal transmits a plurality of data packets to be synchronized, and also a synchronization signal every N said data packets, where N>1, said data packets to be synchronized being transmitted at a frequency which is about constant at least over a period between the transmission of two consecutive synchronization signals.

6. The data synchronization method as claimed in claim 5, in which identification information is introduced into each data packet in correspondence with which a synchronization signal is transmitted, enabling said packet to be associated with the corresponding synchronization signal.

7. The data synchronization method as claimed in claim 5, in which information is introduced into each data packet to be synchronized, enabling an order in which said packets have been transmitted to be determined.

8. The data synchronization method as claimed in claim 1, in which said transmit terminal transmits a single synchronization signal during a data transmission session.

9. The data synchronization method as claimed in claim 1, in which each data packet to be synchronized represents a signal acquired by a sensor or set of sensors associated with said transmit terminal.

10. The data synchronization method as claimed in claim 9, in which each data packet to be synchronized represents a signal generated by a patient in response to a sensory stimulus, said synchronization step (e) comprising the location of said or of each said data packet and said stimulus on a common time base.

11. A data acquisition system to estimate a time of transmission of data packets transmitted between a transmit terminal (TE) and a receive terminal (TR) via a transmission channel ($C_D$), the time of transmission of data corresponding to the time at which the data is transmitted from the transmit terminal (TE), the data propagating from the transmit terminal to the receive terminal with an unknown propagation delay, the data acquisition system comprising:

said one transmit terminal (TE) configured to:
generate at least one synchronization signal ($S_{SYNC}$) having a known temporal relationship with the time of transmission of the data ($S_{EEG}$) to be synchronized, and (a) transmit said data on the transmission channel ($C_D$) to the receive terminal and (b) transmit said synchronization signal on an auxiliary transmission channel ($C_S$) to the receive terminal, the synchronization signal propagating from the transmit terminal to the receive terminal with a known propagation delay; and said receive terminal (TR) configured to:
receive each data packet to be synchronized and the synchronization signal,
synchronize each received data packet using said synchronization signal, and
estimate the time of transmission of the data using the known propagation delay of the synchronization signal and the temporal relationship of the synchronization signal with the time of the transmission.

12. The data acquisition system as claimed in claim 11, in which both said transmission channel and said auxiliary transmission channel are wireless transmission channels.

13. The data acquisition system as claimed in claim 11, in which said transmit terminal is suitable for transmitting a said synchronization signal in correspondence with each said data packet.

14. The data acquisition system as claimed in claim 11, in which said transmit terminal is suitable for transmitting a plurality of data packets to be synchronized, and also a synchronization signal every N said data packets, where N>1, said data packets to be synchronized being transmitted at a frequency which is about constant at least over a period between the transmission of two consecutive synchronization signals.

15. The data acquisition system as claimed in claim 11, also comprising a sensor or set of sensors (RC) associated with said transmit terminal, each data packet transmitted by said or each transmit terminal representing a signal acquired by the corresponding sensor or set of sensors.

16. The data acquisition system as claimed in claim 14, also comprising a sensory stimulation device (DSS) of a patient (P), in which:
said or each sensor or set of sensors is suitable for acquiring neuronal signals representing the response of a patient to a sensory stimulus produced by said stimulation device; and
said receive terminal is suitable for locating each data packet and the said stimulus on a common time base.

* * * * *